United States Patent [19]

Averill et al.

[11] Patent Number: 4,714,472

[45] Date of Patent: Dec. 22, 1987

[54] KNEE PROSTHESIS WITH ACCOMMODATION FOR ANGULAR MISALIGNMENT

[75] Inventors: Robert G. Averill, Ringwood; Alex Khowaylo, Allendale; Christopher G. Sidebotham, Bergenfield, all of N.J.

[73] Assignee: Osteonics Corp., Allendale, N.J.

[21] Appl. No.: 4,525

[22] Filed: Jan. 20, 1987

[51] Int. Cl.[4] .................................................. A61F 2/38
[52] U.S. Cl. .................................................... 623/20
[58] Field of Search .............................. 623/20, 18, 16

[56] References Cited

U.S. PATENT DOCUMENTS

| 3,728,742 | 4/1973 | Averill et al. | 623/20 |
|---|---|---|---|
| 4,081,866 | 4/1978 | Upshaw et al. | 623/20 |
| 4,085,466 | 4/1978 | Goodfellow et al. | 623/20 |
| 4,309,778 | 1/1982 | Buechel et al. | 623/20 |
| 4,568,348 | 2/1986 | Johnson et al. | 623/20 |
| 4,586,933 | 5/1986 | Shoji et al. | 623/20 |

Primary Examiner—Ronald L. Frinks
Attorney, Agent, or Firm—Samuelson & Jacob

[57] ABSTRACT

A knee prosthesis in which articular surface areas of the engaged femoral and tibial components of the prosthesis include surface profile contours lying in a common arcuate profile defined by a medial-lateral radius having an origin lying on the mechanical axis passing through the femoral head of the corresponding hip joint such that limited misalignment of the femoral and tibial components by virtue of angular deviation from the mechanical axis resulting from relative displacement in a medial-lateral direction is tolerated to accommodate the misalignment while maintaining area engagement between the engaged surfaces.

5 Claims, 3 Drawing Figures

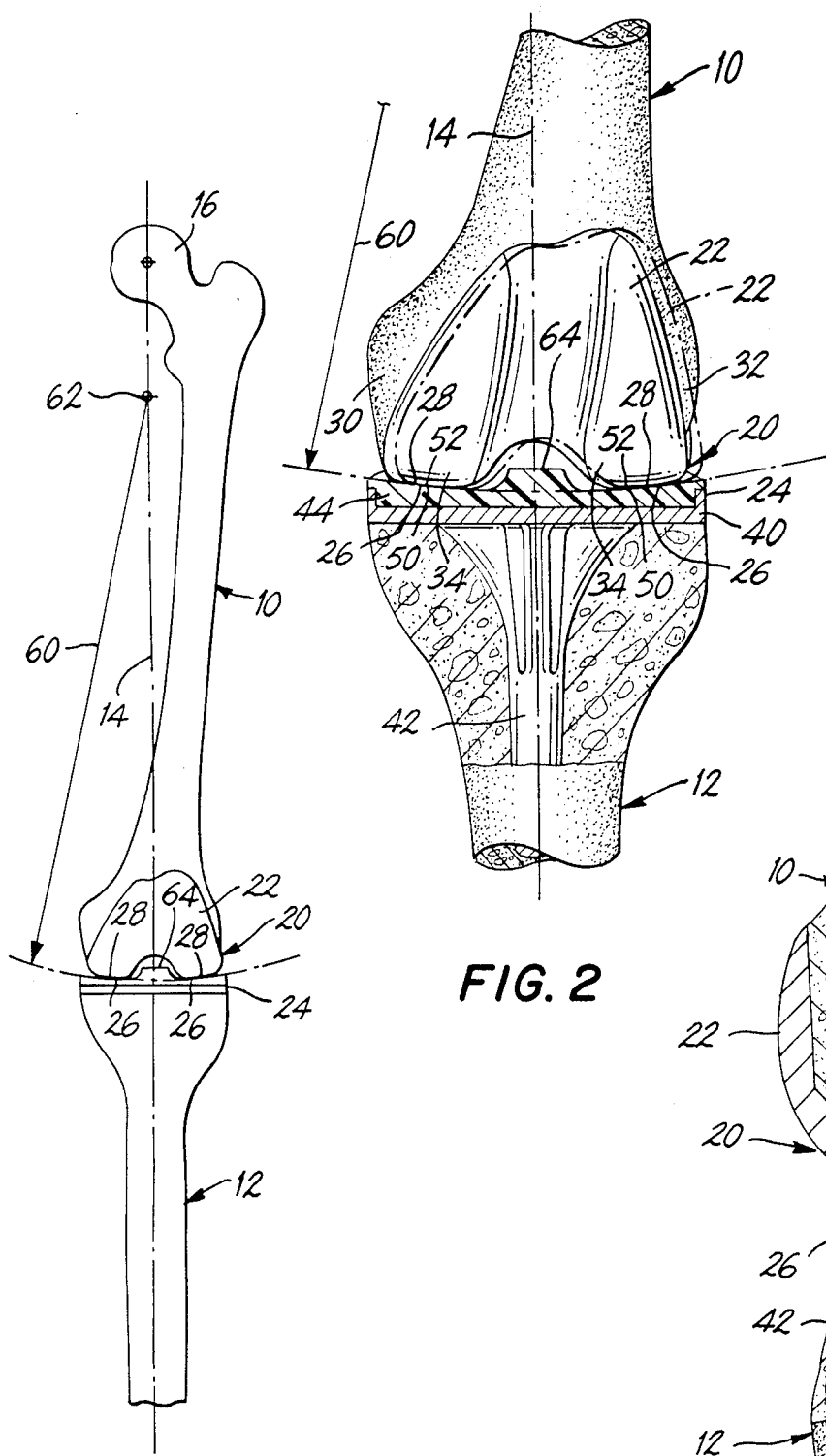
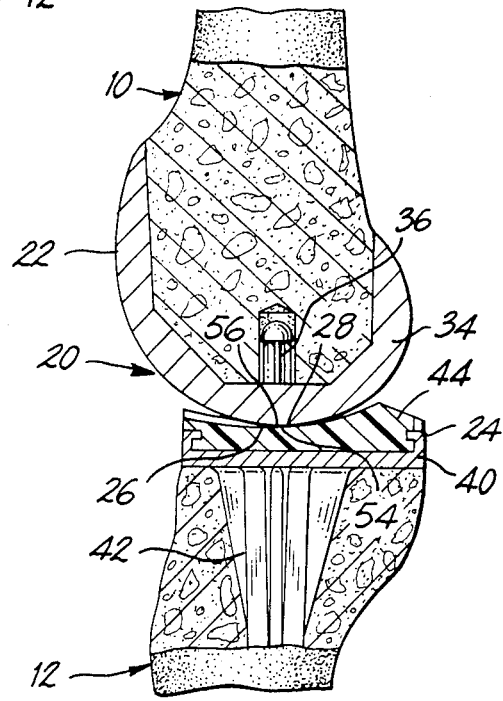
FIG. 1
FIG. 2
FIG. 3

KNEE PROSTHESIS WITH ACCOMMODATION FOR ANGULAR MISALIGNMENT

The present invention relates generally to prosthetic devices used for replacing natural joints in the body and pertains, more specifically, to a knee prosthesis for replacement of the natural knee joint.

The use of prosthetic devices to replace damaged natural joints, or portions of such joints, is becoming more widespread as medical and technological advances are joined to provide improvements facilitating the implant of prosthetic devices which serve as effective substitutes for the natural joints replaced by the devices. However, medical and technical limitations dictate that in most cases prosthetic devices can only simulate and cannot fully duplicate the natural joints replaced by such devices. The effectiveness of a prosthetic device is measured not only by the performance of the implanted prosthesis, but by the ease with which the prosthesis can be implanted so as to realize maximum performance. It becomes necessary, then, in the design and manufacture of a prosthetic device to provide for some latitude in the accuracy of placement of the component parts of the device upon implant as well as to accommodate the various conditions encountered during actual use of the implanted prosthetic device.

Knee protheses have been developed which simulate the articulation of the natural knee joint in that a hinge is provided at the joint between the femur and the tibia. Femoral and tibial components are engaged along articular surfaces which permit articulation similar to that of the natural knee joint. Attempts have been made toward a closer approach to the functions performed by the natural knee joint both in movement and load bearing abilities. One such attempt is disclosed in U.S. Pat. No. 4,085,466 wherein there are described some of the limitations of knee prostheses and an approach toward overcoming these limitations.

The present invention recognizes the exigensies of implant procedures as well as the conditions under which a knee prosthesis must function during the service life of the device and provides a structural arrangement for accommodating these exigencies and conditions. Accordingly, the present invention has several objects and advantages, among which are: the provision of a structural arrangement which accommodates angular misalignments arising out of variations in pre-operative planning, levels of implant skill, and the accuracy of instrumentation utilized in the implant procedure; the provision of a structural arrangement which accommodates misalignments encountered as a result of the dynamics of use of the prosthetic device during the service life thereof; simplicity of design and construction for economy of manufacture and ease of implant; minimum number of component parts for ease of implant as well as for the economy of manufacture; the attainment of optimum performance without the need for exceptional precision in locating and implanting the component parts of the prosthetic device; effective performance of the prosthetic device over a relatively long service life; and ease of manufacture in reasonable quantities of uniform high quality.

The above objects and advantages, as well as further objects and advantages, are attained by the present invention which may be described briefly as an improvement in a knee prosthesis having a femoral component and a tibial component, the tibial component including a bearing member and the femoral component including an arcuate element for confronting and engaging the bearing member to accomplish articulation of the prosthesis, the femoral component and the tibial component ordinarily being aligned axially along a mechanical axis passing through the femoral head of the corresponding hip joint and the engagement between the arcuate element of the femoral component and the bearing member of the tibial component ordinarily taking place along complementary articular surface areas of the arcuate element and the bearing member, the improvement comprising misalignment accommodating means for accommodating limited angular misalignment between the femoral component and the tibial component while maintaining engagement between the arcuate element and the bearing member along complementary articular surface areas, the misalignment accommodating means including complementary medial-lateral surface profile contours along the complementary articular surface areas, the surface profile contours having a medial-lateral articular radius defining an arcuate profile, the origin of which radius lies generally along the mechanical axis such that upon angular misalignment of the femoral component and the tibial component, the resulting relative medial-lateral displacement of the articular surface areas will be accommodated while area engagement between the arcuate element and the bearing member is maintained along the complementary articular surface areas.

The invention will be understood more fully, while still further objects and advantages will become apparent in the following detailed description of an embodiment thereof illustrated in the accompanying drawing, in which:

FIG. 1 is a diagrammatic illustration of a prosthetic implant constructed in accordance with the invention and implanted at the joint between a femur and a tibia;

FIG. 2 is an enlarged fragmentary front elevational view, partially cross-sectioned, of a portion of FIG. 1; and FIG. 3 is a side elevational view, partially cross-sectioned, of the portion shown in FIG. 2.

Referring now to the drawing, and especially to FIG. 1 thereof, a femur 10 and a tibia 12 extend along a mechanical axis 14 which passes through the center of the head 16 of the natural hip joint. The natural knee joint has been replaced by a knee prosthesis 20 constructed in accordance with the invention. Knee prosthesis 20 includes a femoral component 22 affixed to femur 10 and a tibial component 24 affixed to the tibia 12. The femoral component 22 and tibial component 24 provide respective articular surfaces 26 and 28 which engage one another in such a manner as to enable the knee prosthesis 20 to serve as a substitute for the natural knee joint for relative movement of the femur 10 and tibia 12.

Turning now to FIGS. 2 and 3, knee prosthesis 20 is a total knee replacement prosthesis, the femoral component 22 providing a replacement articular surface 26 for each of the medial condyle 30 and the lateral condyle 32 of the femur 10 and the tibial component 24 providing corresponding replacement articular surfaces 28 on the tibia 12. Thus, femoral component 22 is affixed to femur 10 and includes arcuate elements 34 upon which articular surfaces 26 are located. Posts 36 are unitary with arcuate elements 34 and assist in locating the arcuate elements 34, and the articular surfaces 26 thereof, accurately on the femur 10, as well as assisting in the affixation of the femoral component 22 to the femur 10.

Tibial component 24 is affixed to tibia 12 and includes a platform 40 having a unitary depending stem 42 inserted into the tibia 12 to assist in the accurate location and affixation of the platform 40 on the tibia 12. A bearing member 44 is secured in place on platform 40 and provides articular surfaces 28 for engagement by the respective articular surfaces 26 of the femoral component 22 to enable articulation of the knee prosthesis 20. The arcuate elements 34 preferably are constructed of a metal compatible with use in the body, while the preferred material for bearing member 44 is a synthetic resin, such a high-density polyethylene, which provides the articular surfaces 28 with the appropriate lubricity characteristics for the proper functioning of knee prosthesis 20.

In order to enhance the load-bearing capabilities of knee prosthesis 20, and thereby enable higher levels of performance as well as increased longevity and reliability, contact between the articular surfaces 26 and 28 preferably is maintained along complementary areas of the articular surfaces 26 and 28 throughout the range of articulation of the knee prosthesis 20. Thus, articular surfaces 26 and 28 are provided with generally complementary profile contours, both in the medial-lateral plane (the plane of the paper in FIG. 2), as illustrated by complementary profile contours 50 and 52, and in the anterior-posterior plane (the plane of the paper in FIG. 3), as illustrated by complementary profile contours 54 and 56. In this manner, load is spread over articular surface areas and contact stress is reduced.

Ordinarily, femoral component 22 and tibial component 24 are located relative to one another in alignment along the mechanical axis 14 so that the articular surfaces 26 and 28 maintain contact with one another all along the surface extending in the medial-lateral direction. As long as femoral component 22 and tibial component 24 remain in such alignment throughout the range of articulation, contact will be maintained over a sufficient area and stresses along the engaged portions of the articular surfaces 26 and 28 will remain manageable. However, should angular misalignment occur, either as a result of inaccuracies introduced in the implant procedure or as a result of conditions encountered during use of the replacement knee joint, the tendency in previous prosthetic devices is to reduce the area of contact between the engaged portions of the articular surfaces 26 and 28, thereby raising the stresses placed upon the engaged portions. For example, were the profile contours 50 and 52 to be made flat, that is, the profile contours 50 and 52 would lie along straight lines in the medial-lateral plane, the articular surfaces 26 and 28 would remain in line contact all along the medial-lateral direction; however, any angular misalignment would cock the femoral component 22 relative to the tibial component 24, thereby reducing contact between articular surfaces 26 and 28 to a point along the medial-lateral direction and raising considerably the stresses at the point of contact.

Knee prosthesis 20 tolerates limited angular misalignments within the range of misalignment which can result from the conditions outlined above. Thus, the surface profile contours 50 and 52 each follow an arcuate curve having an articular radius 60 in the medial-lateral plane. The center 62, or origin, of the medial-lateral radius 60 lies on the mechanical axis 14, between the knee prosthesis 20 and the femoral head 16. Both the medial and lateral articular surfaces 26 lie along the common surface profile contour 50 defined by the articular radius 60. Likewise, the articular surfaces 28 lie along the common surface profile 52. Slight angular misalignment, as illustrated in phantom in FIG. 2, will result in displacement of one of the components 22 and 24 relative to the other in a medial-lateral direction and such displacement will be accommodated, by virtue of the surface profile contours 50 and 52 assuring that engagement between the articular surfaces 26 and 28 will be maintained over an area of contact, as represented by the illustrated line contact in FIG. 2, and stresses will be held to manageable levels. As best seen in FIG. 2, a central rib 64 is integral with the bearing member 44 and projects upwardly to enter the space between the medial and lateral arcuate elements 34 to provide a stop which limits the medial-lateral articulation of knee prosthesis 20 during use.

It will be apparent that the configuration of the articular surfaces 26 and 28 accommodates limited angular misalignments between the femoral component 22 and the tibial component 24 while maintaining area engagement between the articular surfaces 26 and 28 of arcuate elements 34 and bearing member 44. These misalignments may be the result of variations in pre-operative planning, different levels of implant skill or the accuracy of instrumentation utilized in the implant procedure. Misalignments may occur as a result of conditions encountered during use of the knee prosthesis 20. In any of these events knee prosthesis 20 will accommodate the misalignment without significant reduction in performance or longevity and without a significant increase in complexity and cost.

It is to be understood that the above detailed description of an embodiment of the invention is provided by way of example only. Various details of design and construction may be modified without departing from the true spirit and scope of the invention as set forth in the appended claims.

The embodiments of the invention in which an exclusive property or privilege is claimed are defined as follows:

1. In a knee prosthesis having a femoral component and a tibial component, the tibial component including a bearing member and the femoral component including an arcuate element for confronting and engaging the bearing member to accomplish articulation of the prosthesis, the femoral component and the tibial component ordinarily being aligned axially along a mechanical axis passing through the femoral head of the corresponding hip joint and the engagement between the arcuate element of the femoral component and the bearing member of the tibial component ordinarily taking place along complementary articular surface areas of the arcuate element and the bearing member, the improvement comprising misalignment accommodating means for accommodating limited angular misalignment between the femoral component and the tibial component while maintaining engagement between the arcuate element and the bearing member along complementary articular surface areas, said misalignment accommodating means including complementary medial-lateral surface profile contours along the complementary articular surface areas, said surface profile contours having a medial-lateral articular radius defining an arcuate profile, the origin of which radius lies generally along said mechanical axis such that upon angular misalignment of the femoral component and the tibial component, the resulting relative medial-lateral displacement of the articular surface areas will be accommodated while area engagement between the arcuate element and the bearing member is maintained along said complementary articular surface areas.

2. The invention of claim 1 wherein the origin of the medial-lateral articular radius is located between the articular surface area of the arcuate element and the femoral head.

3. The invention of claim 1 wherein the knee prosthesis provides complementary articular surface areas for both the medial and the lateral condyles of the femur and the improvement includes complementary medial-lateral surface profile contours along the complementary articular surface areas of both condyles, the corresponding surface profile contours of both condyles lying along the arcuate profile defined by the medial-lateral articular radius.

4. The invention of claim 3 wherein the origin of the medial-lateral articular radius is located between the articular surface area of each arcuate element and the femoral head.

5. The invention of claim 3 including a rib extending from the tibial component in position to project between the articular surface areas of the condyles for limiting medial-lateral articulation of the knee prosthesis.

* * * * *